United States Patent [19]

Smith

[11] Patent Number: 5,514,129
[45] Date of Patent: May 7, 1996

[54] AUTOMATIC BIPOLAR CONTROL FOR AN ELECTROSURGICAL GENERATOR

[75] Inventor: Gregory C. Smith, Boulder, Colo.

[73] Assignee: Valleylab Inc., Boulder, Colo.

[21] Appl. No.: 161,737

[22] Filed: Dec. 3, 1993

[51] Int. Cl.[6] ........................................... A61B 17/39
[52] U.S. Cl. ................................ 606/40; 606/38
[58] Field of Search .............................. 606/38, 40, 51

[56] References Cited

U.S. PATENT DOCUMENTS

| | | |
|---|---|---|
| 2,827,056 | 3/1958 | Degelman . |
| 4,860,745 | 8/1989 | Farin . |
| 5,318,563 | 6/1994 | Malis et al. ........................ 606/38 |

FOREIGN PATENT DOCUMENTS

| | | |
|---|---|---|
| 2946728 | 5/1081 | Germany . |
| 1099658 | 2/1961 | Germany . |
| 2540968 | 3/1977 | Germany . |
| 2823291 | 11/1979 | Germany . |
| 3120102 | 12/1982 | Germany . |
| 3510586 | 10/1986 | Germany . |
| 3942998 | 7/1991 | Germany ........................ 606/40 |

*Primary Examiner*—Lee S. Cohen
*Attorney, Agent, or Firm*—Peter C. Richardson; Lawrence C. Akers; Aaron Passman

[57] ABSTRACT

An automatic circuit measures electrosurgical generator output and controls in accord with impedance between activated movable bipolar electrodes able to contact tissue. Voltage monitor in parallel and current monitor in series with the electrodes measure instantaneous variations and generate proportional signals. First and second calculators receive the signals and find respectively, by dividing the voltage by current, short circuit impedances and impedances other than short circuit impedances between the electrodes. First and second comparators receive the respective outputs from the first and second calculators and assess them against respective first and second references providing signs of short conditions and assessments of changes in impedance between the electrodes. A logic analyzer receives the signs and assessments and evaluates them to permit the instantaneous starting, operating or stopping of the electrosurgical generator. The electrodes include an instrument and a set of cables with a preselected combined impedance so the maximum instantaneous impedance between the electrodes is less than the preselected combined impedance. The second reference is user adjustable. Switches, associated with each of the voltage monitor and the current monitor, choose the gain applied to the proportional signals respectively therefrom. First and second calculator gain changers receive the signals for setting the range across which those respective signals are used. Methods have steps of monitoring voltage and current, generating signals, dividing the voltage signal by current signal to find short circuit impedance between the electrodes and the instantaneous changes in impedance for other than the short circuit impedance, assessing those findings against references and permitting the starting, operating, or stopping of the electrosurgical generator.

19 Claims, 2 Drawing Sheets

AUTOMATIC BIPOLAR CONTROL FOR AN ELECTROSURGICAL GENERATOR

1. FIELD OF THE INVENTION

Automatic bipolar control for an electrosurgical generator measures tissue impedance and, in particular, keys the electrosurgical generator during bipolar surgical tissue desiccation. Surgeons find, particularly in bipolar microsurgical procedures, that operator keying by manual hand switching or foot activated switches can cause excessive surgeon body movement resulting in forceps to surgical site displacement.

Surgeons have tried to deal with forceps displacement due to their body movements while manually keying electrosurgical generators by having colleagues key generators after proper forceps placement on patient tissue. Unfortunately, having another surgeon or a nurse key the electrosurgical generator often leads to unintended power delivery or undesired duration of power delivery to the surgical site. Surgeons also experience difficulty in repeatably desiccating tissue to consistent levels due to the limits of human reaction time or machine response time when manual or foot activated switches are used. In addition, during endoscopic procedures, surgeons lose some visual and tactile indications of desiccation progression.

2. BACKGROUND OF THE DISCLOSURE

As a result of manual operation problems, several attempts to provide automatic generator operation when surgical forceps contact patient tissue have been patented. U.S. Pat. No. 2,827,056, German patent 1,099,658, German patent 28 23 291 describe circuits which place a direct current potential across the surgical forceps. Placement of the forceps across patient tissue causes a small DC current to flow therethrough. Direct current flow causes activation of a relay circuit enabling the higher power radio frequency energy to flow into the patient's tissue for surgical effect. Selecting fixed resistance values, within the circuits, determine the tissue impedance level below which radio frequency energy activation occurs.

Patent German Patent DE 25 40 968 describes a circuit which uses a low-frequency measurement current to determine relative patient tissue impedance; low frequency current flow within a specified amplitude range turns on generator high frequency power for surgical effect. That circuit also includes a time delay relay for controlling time between application of forceps to patient tissue and subsequent generator keying.

Subsequent patents addressed the need for automatic turn off capability during bipolar desiccation procedures. German patent DE 31 20 102 A1 describes a circuit which monitors the differential quotient (time derivative) of patient tissue impedance to determine when to turn off radio frequency power delivery; the inventor selects the point of zero time derivative to turn off power delivery. German patent DE 29 46 728 A1 describes a circuit which turns radio frequency power off after an adjustable, but fixed time delay. German patent DE 35 10586 describes a circuit which uses a low-frequency control current or low level generator radio frequency current source and a current level monitor to turn on generator radio frequency power for surgical effect. The circuit also monitors the generator output voltage for third harmonic content generated when desiccation completes and sparking begins to cause harmonic frequency generation to turn off generator radio frequency power.

U.S. Pat. No. 4,860,745 discusses the problems encountered when turning off radio frequency power based upon measurements of the time derivative of patient tissue impedance and, instead, presents a circuit which turns off generator radio frequency power based upon fixed fractional changes in the amount of radio frequency current delivered to the patient tissue during desiccation or based upon generator sparking and harmonic frequency generation.

No circuitry has been known to avoid inadvertent turn off due to varying time derivative of tissue impedance and to provide more consistent desiccation levels than possible when turning radio frequency power off after a fixed time interval or when measuring fixed fractional changes in the amount of radio frequency current delivered to the patient tissue.

SUMMARY OF THE INVENTION

The disclosure herein has a circuit which measures absolute patient tissue impedance. Studies conducted show that, in spite of initial tissue impedance, tissue desiccation tends to complete at about the same impedance level. The control turns generator radio frequency power on if patient tissue impedance lies within a preset range and turns generator radio frequency power off if tissue impedance falls too low (to protect against keying into short circuited forceps) or if tissue impedance increases to the absolute impedance level required to indicate desired desiccation level. The control uses low level radio frequency power to sense patient tissue impedance after the user applies forceps to the patient tissue, but before the generator keys, and monitors generator radio frequency voltage and current to sense patient tissue impedance when the generator is keyed.

An automatic circuit measures electrosurgical generator output and controls it in accord with impedance between activated bipolar electrodes attached thereto. A pair of spaced apart bipolar electrodes are preferably able to move together and apart for contacting tissue therebetween. A voltage monitor in parallel with the pair of bipolar electrodes may measure the instantaneous voltage variations therebetween and generate proportional signals relative to the instantaneous variations of voltage.

A current monitor in series with the pair of bipolar electrodes may measure the instantaneous current variations therebetween and generate proportional signals relative to the instantaneous variations of current. A first calculator attached to the voltage monitor and the current monitor preferably receives the proportional signals to instantaneously find by in effect dividing the voltage by current to obtain the instantaneous indications of short circuit impedances between the pair of bipolar electrodes. A second calculator attached to the voltage monitor and the current monitor preferably receives the proportional signals to instantaneously find by in effect dividing the voltage by current to obtain the instantaneous changes in impedances between the bipolar electrodes for other than short circuit impedance.

A first comparator connected to receive the output from the first calculator may assess instantaneously the output against a first reference for providing instantaneous signs identifying short conditions between the pair of bipolar electrodes. A second comparator connected to receive the output from the second calculator may assess instantaneously the output against a second reference for providing assessments of the instantaneous indications of changes in impedance between the pair of bipolar electrodes. A logic analyzer for receiving the signs and assessments of the first and second comparators most preferably evaluates the signs and assessments to permit the instantaneous starting, operating or stopping of the electrosurgical generator based on the evaluation.

The pair of bipolar electrodes may include a bipolar instrument and a set of cables; the set of cables connects between the electrosurgical generator and the bipolar instrument. The bipolar instrument and the set of cables may have a preselected combined impedance and wherein the maximum instantaneous impedance between the pair of bipolar electrodes as found instantaneously by the second calculator is significantly less than the preselected combined impedance of the set of cables and the instrument so that the preselected combined impedance does not mask changes in the measured impedance between the pair of bipolar electrodes.

The maximum instantaneous impedance between the pair of bipolar electrodes as found instantaneously by the second calculator and the preselected combined impedance are preferably different by at least a factor of one hundred and fifty percent so that the instantaneous impedance between the pair of bipolar electrodes is significantly less than the preselected combined impedance of the set of cables and the instrument to prevent masking changes in the measured impedance between the pair of bipolar electrodes.

The preselected combined impedance has preferably a total value of greater than about one hundred and fifty percent of the maximum instantaneous impedance between the pair of bipolar electrodes. The total value is preferably a result of the predetermined combined characteristic impedances of the bipolar instrument and the preselected set of cables and further that either the impedance of the set of cables or the bipolar instrument or the pair of bipolar electrodes can be chosen to obtain the factor. The second reference may be set by an adjuster which affects a variable threshold device as the second reference. The adjuster may be a potentiometer that influences an adjustable diode which establishes a variable threshold above which current is permitted to flow through the adjustable diode as the second reference. Switches, associated with each of the voltage monitor and the current monitor, may choose the gain applied to the proportional signals respectively therefrom.

The first and second calculators each might preferably include a gain changer connected to receive the proportional signals therefrom for setting the range across which those respective signals are useful for acceptable automatic operation by use of instantaneously calculated impedance. The preselected set of cables may have a connector for conjugating with the electrosurgical generator output and allowing only the preselected set of cables to operate the electrosurgical generator. A control in circuit with the electrosurgical generator output may preferably delay activation thereof from zero to several seconds.

A method for automatically measuring and controlling the electrosurgical generator output in accord with impedance between activated bipolar electrodes may include the steps of holding the pair of bipolar electrodes able to move together and apart to contact tissue therebetween. The next step may be monitoring voltage in the circuit parallel with the pair of bipolar electrodes for measuring the instantaneous voltage variations therebetween. That is followed by the step of generating proportional voltage signals relative to the instantaneous voltage variations thereof and monitoring current in a circuit in series with the pair of bipolar electrodes for measuring the instantaneous current variations therebetween. Then the step of generating proportional signals relative to the instantaneous current variations thereof follows. The step of dividing the instantaneous proportional voltage signal by the instantaneous proportional current signal may obtain instantaneous indications of short circuit impedance between the pair of bipolar electrodes with the first calculator. The step of dividing the proportional instantaneous voltage signal by the instantaneous proportional current signal may obtain the instantaneous changes in impedance for other than the short circuit impedance with the second calculator. Instantaneously assessing the output from the first calculator against the first reference preferably provides instantaneous signals identifying short conditions between the pair of bipolar electrodes and assessing instantaneously the output from the second calculator against the second reference preferably provides instantaneous indications of changes in impedance between the pair of bipolar electrodes, thus permitting the starting, operating, or stopping of the electrosurgical generator based on evaluating signs and assessments of the first and second comparators by the logic analyzer.

The method may have the step of maintaining the maximum instantaneous impedance between the pair of bipolar electrodes as found instantaneously by the second calculator at a value significantly less than the preselected combined impedance of the pair of bipolar electrodes consisting of the bipolar instrument and the set of cables which prevents masking changes and enables accurately measuring impedance between the pair of bipolar electrodes. The method may further include the step of maintaining that the preselected combined impedance of the pair of bipolar electrodes remains at about a factor one hundred and fifty percent of the instantaneous impedance measured between the pair of bipolar electrodes so that the instantaneous impedance measured is significantly less than the preselected combined impedance of the cables and the instrument. The method preferably has the step of adjusting the second reference to influence the adjustable diode which establishes the variable threshold above which current is permitted to flow therethrough as a second reference.

The method might include the step of setting the range for which the proportional signals are useful for acceptable automatic operation with the gain changer connected to receive the proportional signals. The method step of conjugating the preselected set of cables with the electrosurgical generator output may allow only the preset cables to operate with the electrosurgical generator. The method might preferably have the step of delaying the activation of the automatic control circuit by holding the electrosurgical generator output for a period in the range of about zero to several seconds.

The automatic control automatically, instantaneously and continuously may monitor electrosurgical generator output voltage and output current and, through two impedance measurement circuits, might provide, if desired, two direct current voltages proportional to patient tissue impedance. One circuit may be tuned to measure, with a high degree of accuracy, very low tissue impedances (below 50 ohms), while another second circuit may be tuned to measure, with excellent accuracy, high tissue impedances (above 500 ohms). The automatic control preferably uses tissue impedance measurements made in real time to turn on and turn off the electrosurgical generator output power at the predefined appropriate patient tissue impedance levels.

For controllability, the invention may also provide, by interface to a microprocessor, gain switching of circuit amplifiers and techniques for calibrating or altering circuit hardware divider gain during operation. Additional features under microprocessor control may preferably include the user adjustable potentiometer for setting generator RF turn on delay and the cables detection circuit for ensuring that users only have feature compatible controlled impedance accessory cables. Due to circuit interface to an electrosurgical generator microprocessor, the automatic control may have microprocessor software to execute the control functions. The automatic control may compare measured low impedance direct current output voltage and measured high impedance direct current output voltage to reference voltages and when within predefined ranges turn the electrosurgical generator radio frequency power either on or off.

DETAILED DESCRIPTION OF THE INVENTION

Figure 1:
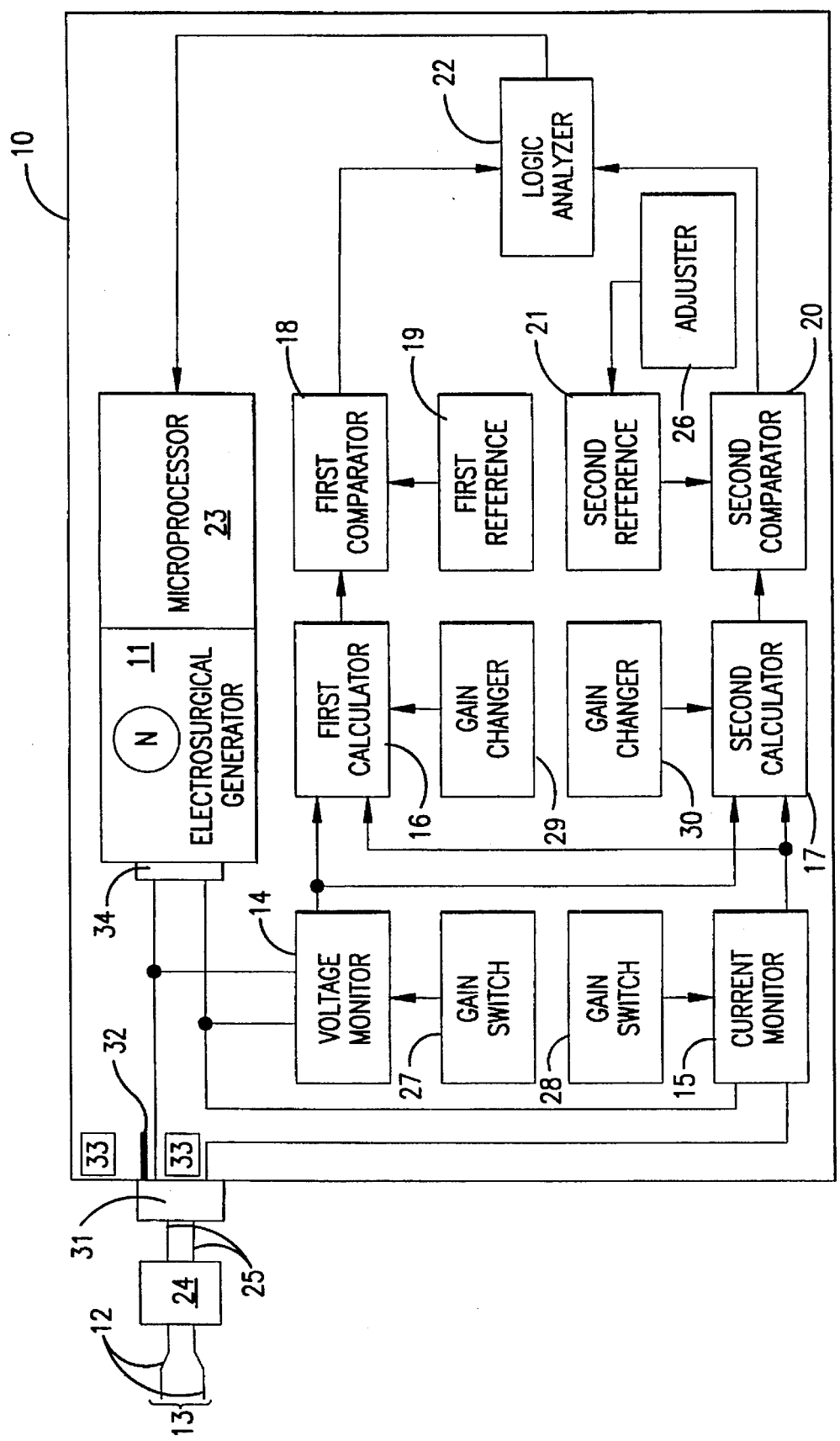
FIG. 1 shows a schematic block diagram of the automatic circuit for measuring tissue desiccation between bipolar electrodes connected to an electrosurgical generator output and the circuit controls the output in accord with impedance between the electrodes.

An automatic circuit 10 as shown in FIG. 1 measures an electrosurgical generator 11 output and controls it in accord with impedance between activated bipolar electrodes 12 attached thereto. A pair 13 of the spaced apart bipolar electrodes 12 are in the preferred embodiment opposed forceps but can be a scissors or any other bipolar instrument which has electrosurgical electrodes able to move together and apart for contacting tissue to be desiccated therebetween.

A voltage monitor 14 in parallel with the pair 13 of bipolar electrodes 12 measures the instantaneous voltage variations therebetween and generates proportional signals relative to the instantaneous variations of voltage. A capacitor divider in circuit or transformer that is inductively sensitive to instantaneous variations in voltage between two lines of the automatic circuit is used as the voltage monitor 14.

A current monitor 15 in series with the pair 13 of bipolar electrodes 12 measures the instantaneous current variations therebetween and generate proportional signals relative to the instantaneous variations of current. An inductive transformer is used to couple with the part of the automatic circuit wherein the instantaneous current value is desired in the preferred embodiment as the current monitor 15.

A first calculator 16 attached to the voltage monitor 14 and the current monitor 15 receives their respective proportional signals to instantaneously find by in effect dividing the voltage by current to obtain the instantaneous indications of short circuit impedances between the pair 13 of bipolar electrodes 12. A combination of two RMS to direct current converters preferably, Analog Devices of Massachusetts, AD637, one for voltage and another for current, are each used with an integrated circuit hardware divider, Analog Devices AD734.

A second calculator 17 attached to the voltage monitor 14 and the current monitor 15 receives their respective proportional signals to instantaneously find by in effect dividing the voltage by current to obtain the instantaneous changes in impedances between pair 13 of the bipolar electrodes 12 for other than short circuit impedance. Analogue Devices' components similar to those used for the first calculator 16 are also applied here for the second calculator 17.

A first comparator 18 connected to receive the output from the first calculator 16 assesses instantaneously the output against a first reference 19 for providing instantaneous signs identifying short conditions between the pair 13 of bipolar electrodes 12. An integrated circuit is preferred for use for the comparison function, i.e., National Semiconductor, California, LM393. A second comparator 20 connected to receive the output from the second calculator 17 assesses instantaneously the output against a second reference 21 for providing assessments of the instantaneous indications of changes in impedance between the pair 13 of bipolar electrodes 12. Similarly an integrated circuit is preferably used, such as National Semiconductor LM393.

A logic analyzer 22 for receiving the signs and assessments of the first and second comparators 18 and 20 evaluates the signs and assessments to permit the instantaneous starting, operating or stopping of the electrosurgical generator based on the evaluation. The logic circuit 22 is in the preferred embodiment a wired OR connection of the instantaneous outputs from the first and second comparators 18 and 20 but can be code in a microprocessor or any other electronic circuit that has an OR function. The instantaneous starting, operating or stopping of the electrosurgical generator 11 is accomplished by code in a microprocessor 23 in the electrosurgical generator 11. For example, the Force IRS series electrosurgical generator 11 by Valleylab of Boulder, Colo., has a Intel 80C196 microprocessor 23 which among other functions handles this control as well.

The pair 13 of bipolar electrodes 12 may be a bipolar instrument 24, as an example, Valleylab E700.292 Bipolar Forceps and a set of cables, as an example, Valleylab E0719 Autobipolar Cable; the set of cables 25 connects between the electrosurgical generator 11 and the bipolar instrument 24. The bipolar instrument 24 and the set of cables 25 has a preselected combined impedance. The maximum instantaneous impedance between the pair 13 of bipolar electrodes 12 as found instantaneously by the second calculator 17 is in the preferred embodiment significantly less than the preselected combined impedance of the set of cables 25 and the instrument 24 so that the preselected combined impedance does not mask changes in the measured impedance between the pair 13 of bipolar electrodes 12.

In operation, the maximum instantaneous impedance between the pair 13 of bipolar electrodes 12 as found instantaneously by the second calculator 17 and the preselected combined impedance are different by at least a factor of one hundred and fifty percent. Thus, the instantaneous impedance between the pair 13 of bipolar electrodes 12 is significantly less than the preselected combined impedance of the set of cables 25 and the instrument 24 to prevent masking changes in the measured impedance between the pair 13 of bipolar electrodes 12.

The preselected combined impedance has a total value of greater than about one hundred and fifty percent of the maximum instantaneous impedance between the pair 13 of bipolar electrodes 12. The total value is, as explained, a result of the predetermined combined characteristic impedances of the bipolar instrument 24 and the preselected set of cables 25. Either the impedance of the set of cables 25 or the bipolar instrument 24 or the pair 13 of bipolar electrodes 12 can be chosen to obtain the desired factor.

The second reference 21 is set by an adjuster 26 which affects a variable threshold device as the second reference. The adjuster 26 can be a potentiometer that influences an adjustable diode, e.g., National Semiconductor LM336-5.0 which establishes a variable threshold above which current is permitted to flow through the adjustable diode as the second reference. Gain switches 27 and 28 for voltage and current monitors 14 and 15, respectively are preferably Siliconix DG445 integrated circuit analog switches. The gain switches 27 and 28 choose the gain applied via operational amplifier circuits, Analog Devices AD848 and AD827, to the proportional signals respectively received therefrom.

The first and second calculators 16 and 17 each include a gain changer 29 and 30, respectively, connected to receive the proportional signals therefrom for setting the range across which those respective signals are useful for acceptable automatic operation by use of instantaneously calculated impedance. The preferred gain changes 29 and 30 are Analog Devices AD734 hardware multipliers have built-in gain changers and gain changer inputs on the AD734 may be driven, for example, by a Phillips TDA8444 digital-to-analog converter integrated circuit connected to the electrosurgical generator microprocessor.

The preselected set of cables 25 have a special custom made connector 31 for conjugating with the electrosurgical generator 11 output and allowing only the preselected set of cables 25 to operate the electrosurgical generator 11. The connector 31 has a non-electrically connected metal pin 32 added thereto which conjugates with the receptacle of the electrosurgical generator 11 and is detected by a light emitting diode/phototransistor pair 33 preferably Optek OPB703. Any similar arrangement which will identify the non-electrically connected metal pin 32 is acceptable to recognize the special connector 31 in place and so the preselected combined impedance set applied.

A control 34 in circuit with the electrosurgical generator 11 output delays activation thereof from zero to several seconds. A variable resistance potentiometer in a voltage divider circuit may be used to provide a control voltage to the microprocessor for establishing the delay.

A method for automatically measuring and controlling the electrosurgical generator 11 output in accord with impedance between the pair 13 of activated bipolar electrodes 12 includes the step of holding the pair 13 of bipolar electrodes 12 able to move together and apart to contact tissue therebetween. The next method step provides for monitoring voltage in the circuit parallel with the pair 13 of bipolar electrodes 12 for measuring the instantaneous voltage variations therebetween. That is followed by the step of generating proportional voltage signals relative to the instantaneous voltage variations thereof and monitoring current in a circuit in series with the pair 13 of bipolar electrodes 12 for measuring the instantaneous current variations therebetween. Then the step of generating proportional signals relative to the instantaneous current variations thereof follows. The step of dividing the instantaneous proportional voltage signal by the instantaneous proportional current signal obtains instantaneous indications of short circuit impedance between the pair 13 of bipolar electrodes 12 with the first calculator 16. The step of dividing the proportional instantaneous voltage signal by the instantaneous proportional current signal calculates the instantaneous changes in impedance for other than the short circuit impedance with the second calculator 17. Instantaneously assessing the output from the first calculator 16 against the first reference 19 preferably provides instantaneous signals identifying short conditions between the pair 13 of bipolar electrodes 12 and assessing instantaneously the output from the second calculator 17 against the second reference 21 provides instantaneous indications of changes in impedance between the pair 13 of bipolar electrodes 12, thus permitting the starting, operating, or stopping of the electrosurgical generator 11 based on evaluating signs and assessments of the first and second comparators 18 and 20 by the logic analyzer 22.

The method has the step of maintaining the maximum instantaneous impedance between the pair 13 of bipolar electrodes 12 as found instantaneously by the second calculator 17 at a value significantly less than the preselected combined impedance of the pair 13 of bipolar electrodes 12 as the bipolar instrument 24 and the set of cables 25 which prevents masking changes and enables accurately measuring impedance between the pair 13 of bipolar electrodes 12. The method further includes the step of maintaining that the preselected combined impedance of the pair 13 of bipolar electrodes 12 remains at about a factor one hundred and fifty percent of the instantaneous impedance measured between the pair 13 of bipolar electrodes 12 so that the instantaneous impedance measured is significantly less than the preselected combined impedance of the cables 25 and the instrument 24. The method has the step of adjusting the second reference 21 to influence the adjuster 26, preferably an adjustable diode which establishes the variable threshold above which current is permitted to flow therethrough as a second reference 21.

The method includes the step of setting the range for which the proportional signals are useful for acceptable automatic operation with the gain changers 29 and 30 connected to receive the proportional signals. The method step of conjugating the preselected set of cables 25 with the electrosurgical generator 11 output allows only those set of cables 25 to operate with the electrosurgical generator 11. The method has the step of delaying the activation of the automatic control circuit by holding the electrosurgical generator 11 output for a period in the range of about zero to several seconds.

The automatic control automatically, instantaneously and continuously monitors electrosurgical generator 11 output voltage and output current and, through two impedance measurement circuits, might provide, if desired, two direct current voltages proportional to patient tissue impedance. One circuit is tuned to measure, with a high degree of accuracy, very low tissue impedances below 50 ohms, while another second circuit is tuned to measure, with excellent accuracy, high tissue impedances above 500 ohms. The automatic control preferably uses tissue impedance measurements made in real time to turn on and turn off the electrosurgical generator output power at the predefined appropriate patient tissue impedance levels.

For controllability, the invention also provides, by interface to the microprocessor 23, gain switching of circuit amplifiers and techniques for calibrating or altering circuit hardware divider gain during operation. Additional features under microprocessor control includes the user adjustable potentiometer, control 34, for setting generator RF turn on delay and the set of cables 25 detection circuit for ensuring that users only have feature compatible controlled impedance accessory set of cables 25. Due to circuit interface to the electrosurgical generator 11 microprocessor 23, the automatic control has microprocessor software to execute the control functions. The automatic circuit 10 compares measured low impedance direct current output voltage and measured high impedance direct current output voltage to reference voltages and when within predefined ranges turns the electrosurgical generator 11 radio frequency power either on or off.

Figure 2:
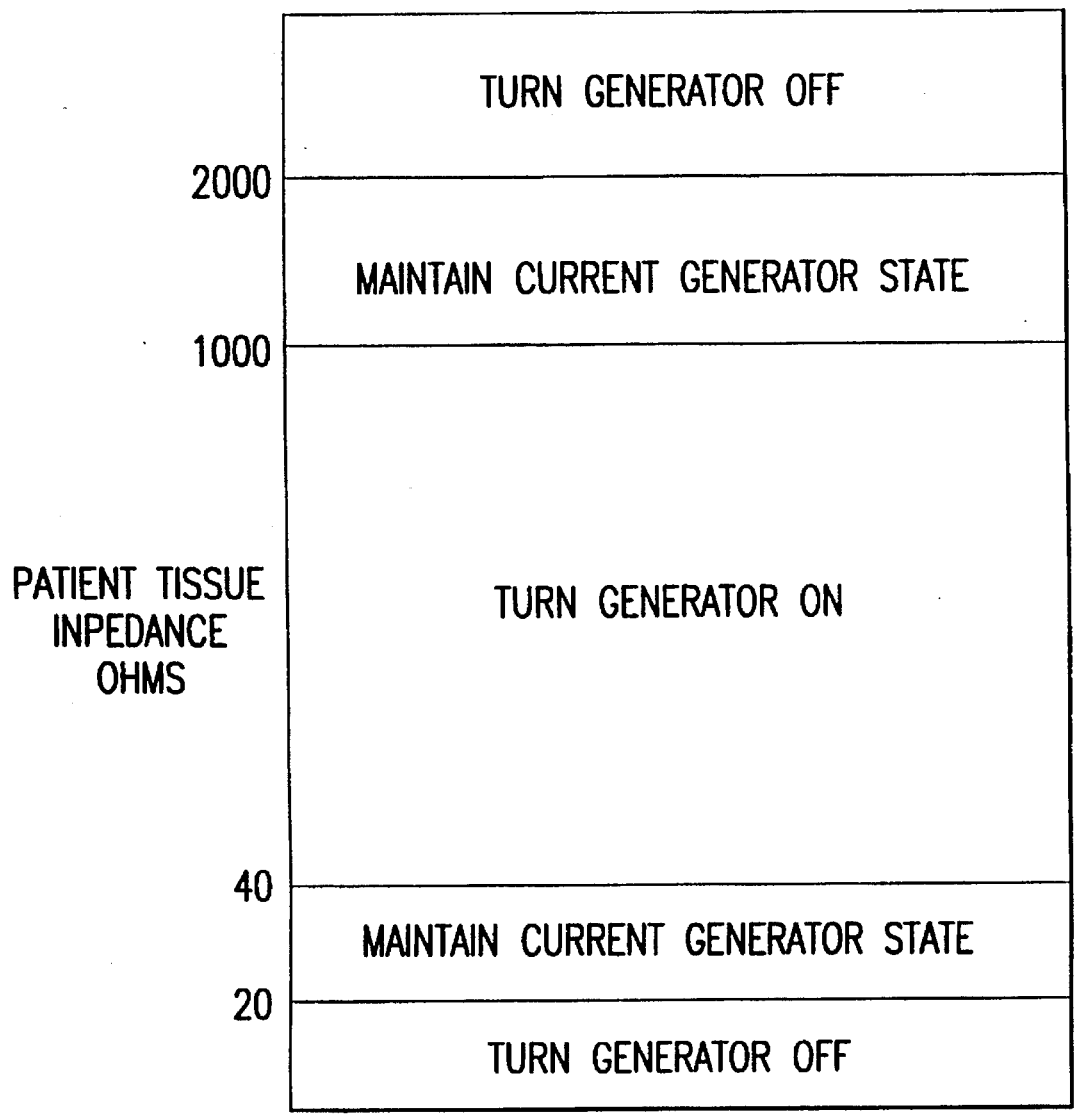
FIG. 2 is a chart showing the preferred patient tissue impedance settings for turning an electrosurgical generator on and off.

FIG. 2 is a chart showing the preferred patient tissue impedance settings for generator 11 turn-on and turn-off. The automatic circuit 10, in preferred embodiment, turns electrosurgical generator 11 power on when a user applies bipolar instrument 24 to patient tissue and tissue impedance lies between 40 and 1000 ohms. Once electrosurgical generator 11 radio frequency power is on, the automatic circuit turns electrosurgical generator 11 power off when tissue impedance is greater than 2000 ohms or when tissue impedance is less than 20 ohms. Therefore, the automatic circuit 10 will not key the electrosurgical generator 11 into short-circuited forceps.

What is claimed is:

1. An automatic circuit that measures electrosurgical generator output and controls it in accord with impedance between activated bipolar electrodes attached thereto, comprising:

an electrosurgical generator;

a pair of spaced apart bipolar electrodes able to move together and apart for contacting tissue therebetween connected to the electrosurgical generator;

a voltage monitor connected in parallel with the pair of bipolar electrodes for measuring an instantaneous voltage variation therebetween and generating proportional signals relative to each measured instantaneous variation of voltage;

a current monitor connected in series with the pair of bipolar electrodes for measuring an instantaneous current variation therebetween and generating proportional signals relative to each measured instantaneous variation of current;

a first calculator attached to the voltage monitor and the current monitor for receiving the proportional signals to find by in effect dividing the voltage by current for generating proportional signals relative to the instantaneous indications of short circuit impedances between the pair of bipolar electrodes;

a second calculator attached to the voltage monitor and the current monitor for receiving the proportional signals to find by in effect dividing the voltage by current for generating proportional signals relative to the instantaneous changes in impedances between the pair of bipolar electrodes for other than short circuit impedance;

a first comparator connected to receive the proportional signals from the first calculator, assess these proportional signals against a first reference and provide instantaneous signs identifying short conditions between the pair of bipolar electrodes;

a second comparator connected to receive the proportional signals from the second calculator, assess these proportional signals against a second reference and provide assessments of the instantaneous signs identifying changes in impedance between the pair of bipolar electrodes; and a logic analyzer connected to receive the signs and assessments of the first and second comparators and to control the electrosurgical generator for evaluating the signs and assessments to permit the starting, operating or stopping of the electrosurgical generator based on the evaluation.

2. The automatic circuit for an electrosurgical generator of claim 1 wherein the pair of bipolar electrodes further includes a bipolar instrument and a set of cables, the set of cables connect between the electrosurgical generator and the bipolar instrument, the bipolar instrument and the set of cables having a preselected combined impedance and wherein a maximum instantaneous impedance between the pair of bipolar electrodes as found by the second calculator is significantly less than the preselected combined impedance of the set of cables and the instrument so that the preselected combined impedance does not mask changes in the measured impedance between the pair of bipolar electrodes.

3. The automatic circuit for an electrosurgical generator of claim 2 wherein the maximum instantaneous impedance between the pair of bipolar electrodes as found by the second calculator and the preselected combined impedance differ by at least about one hundred and fifty percent so that the maximum instantaneous impedance between the pair of bipolar electrodes is significantly less than the preselected combined impedance to prevent masking changes in the measured impedance between the pair of bipolar electrodes.

4. The automatic circuit for an electrosurgical generator of claim 2 wherein the preselected combined impedance is greater than about one hundred and fifty percent of the maximum instantaneous impedance between the pair of bipolar electrodes.

5. The automatic circuit for an electrosurgical generator of claim 4 wherein the preselected combined impedance is a result of selecting the impedance of either the set of cables or the bipolar instrument or the pair of bipolar electrodes.

6. The automatic circuit for an electrosurgical generator of claim 5 wherein the set of cables includes a connector for conjugating with the electrosurgical generator output and allowing only the set of cables to operate the electrosurgical generator.

7. The automatic circuit for an electrosurgical generator of claim 1 wherein the second reference is connected to an adjuster for setting a variable threshold device in the second reference.

8. The automatic circuit for an electrosurgical generator of claim 7 wherein the adjuster consists of a potentiometer connected to an adjustable diode which establishes a variable threshold above which current is permitted to flow through the adjustable diode.

9. The automatic circuit for an electrosurgical generator of claim 1 wherein the voltage monitor and the current monitor each include a gain switch connected to receive and influence the proportional signals therefrom.

10. The automatic circuit for an electrosurgical generator of claim 1 wherein the first and second calculators each include a gain changer connected to receive the proportional signals therefrom for setting a range across which those respective signals are useful for acceptable automatic operation of the electrosurgical generator.

11. The automatic circuit for an electrosurgical generator of claim 1 wherein a control in circuit with the electrosurgical generator output delays activation thereof from zero to several seconds.

12. A method for automatically measuring and controlling an output from an electrosurgical generator in accord with impedance between a pair of activated bipolar electrodes attached thereto, including the following steps:

holding a pair of bipolar electrodes able to move together and apart to contact tissue therebetween;

monitoring voltage levels in a circuit connected in parallel with the pair of bipolar electrodes by measuring each instantaneous voltage variation therebetween;

generating proportional voltage signals relative to each instantaneous voltage variation thereof;

monitoring current levels in a circuit connected in series with the pair of bipolar electrodes by measuring each instantaneous current variation therebetween;

generating proportional signals relative to each instantaneous current variation thereof;

dividing the instantaneous proportional voltage signal by the instantaneous proportional current signal to obtain instantaneous indications of short circuit impedance between the pair of bipolar electrodes;

dividing the proportional instantaneous voltage signal by the instantaneous proportional current signal to obtain instantaneous indications of impedance for other than the short circuit impedance;

assessing the instantaneous indications of short circuit impedance against a first reference for providing instantaneous signals identifying short circuit conditions between the pair of bipolar electrodes;

assessing the instantaneous indications of impedance for other than short circuit impedance against a second reference for providing instantaneous indications of other than short circuit conditions between the pair of bipolar electrodes; and permitting the starting, operating, or stopping of the electrosurgical generator based on evaluating the indications of short circuit conditions and of impedance for other than short circuit conditions by a logic analyzer.

13. The method of claim 12 further including a step of maintaining a maximum instantaneous impedance between the pair of bipolar electrodes at a value significantly less than a preselected combined impedance of a pair of bipolar electrodes further consisting of a bipolar instrument and a set of cables.

14. The method of claim 13 wherein the step of maintaining the maximum instantaneous impedance between the pair of bipolar electrodes requires maintaining the maximum instantaneous impedance at about one hundred and fifty percent of the preselected combined impedance.

15. The method of claim 12 further including a step of adjusting the second reference to establish a variable threshold above which current is permitted to flow therethrough as a second reference.

16. The method of claim 12 further including the step of setting a range for acceptable automatic electrosurgical generator operation by adjusting a gain changer.

17. The method of claim 12 further including a step of conjugating a preselected set of cables with the electrosurgical generator output wherein only the preselected set of cables are allowed to operate with the electrosurgical generator.

18. The method of claim 12 further including a step of delaying the activation of the electrosurgical generator output for about zero to several seconds with a control in circuit with the electrosurgical generator.

19. An automatic circuit that measures electrosurgical generator output and controls it in accord with impedance between activated bipolar electrodes attached thereto, comprising:

an electrosurgical generator;

a pair of spaced apart bipolar electrodes able to move together and apart for contacting tissue therebetween and wherein the pair of bipolar electrodes includes a bipolar instrument and a set of cables, the set of cables connect between the electrosurgical generator and the bipolar instrument, the bipolar instrument and the set of cables having a preselected combined impedance;

a voltage monitor connected in parallel with the pair of bipolar electrodes for measuring each instantaneous voltage variation therebetween and generating proportional signals relative to each instantaneous variation of voltage;

a current monitor connected in series with the pair of bipolar electrodes for measuring instantaneous current variations therebetween and generating proportional signals relative to each instantaneous variation of current;

gain switches connected to the voltage monitor and the current monitor choose the amount of gain applied to the proportional signals respectively therefrom;

a first calculator attached to the voltage monitor and the current monitor for receiving the proportional signals to find by in effect dividing the voltage by current and generate indications of short circuit impedance between the pair of bipolar electrodes;

a second calculator attached to the voltage monitor and the current monitor for receiving the proportional signals to find by in effect dividing the voltage by current and generate indications of other than short circuit impedance between the bipolar electrodes;

gain changers in each of the first and second calculators, the gain changer connected to receive the proportional signals there from for setting a range across which those respective signals are useful for acceptable automatic electrosurgical generator operation;

a first comparator connected to receive the indications of short circuit impedance from the first calculator and an output from a first reference for assessing and generating instantaneous signs identifying short circuit conditions between the pair of bipolar electrodes;

a second comparator connected to receive the indications of other than short circuit impedance from the second calculator and an output from a second reference for assessing and generating instantaneous signs of changes in impedance between the pair of bipolar electrodes and wherein the second reference is set by an adjuster which affects a variable threshold device in the second reference and wherein the adjuster is a potentiometer and the variable threshold device is an adjustable diode;

wherein the maximum instantaneous impedance between the pair of bipolar electrodes as found instantaneously by the second calculator is significantly less than a preselected combined impedance of a set of cables and a bipolar instrument so that the preselected combined impedance does not mask measured changes in impedance between the pair of bipolar electrodes and wherein the maximum instantaneous impedance differs by about one hundred and fifty percent so that impedance measured between the pair of bipolar electrodes is significantly less than the preselected combined impedance to prevent masking changes in the measured impedance between the pair of bipolar electrodes or wherein the preselected combined impedance is greater than one hundred and fifty percent of the maximum instantaneous impedance between the pair of bipolar electrodes relative to measured variations of voltage and wherein the preselected combined characteristic impedance is a result of selecting the impedance of either the set of cables or the bipolar instrument or the pair of bipolar electrodes;

wherein the preselected set of cables includes a connector for conjugating with the electrosurgical generator output and allowing only the preselected set of cables to operate the electrosurgical generator;

wherein a control in circuit with the electrosurgical generator output delays activation thereof from zero to several seconds; and a logic analyzer connected to receive the signs and assessments of the first and second comparators and to control the electrosurgical generator for evaluating the signs and assessments to permit the starting, operating or stopping of the electrosurgical generator based on the evaluation.

* * * * *